US008855779B2

(12) United States Patent
Afargan et al.

(10) Patent No.: US 8,855,779 B2
(45) Date of Patent: Oct. 7, 2014

(54) METHODS OF DIAGNOSIS AND TREATMENT OF WOUNDS, METHODS OF SCREENING FOR ELECTRICAL MARKERS FOR WOUNDS PROGNOSIS IN PATIENTS

(75) Inventors: Michel Afargan, Ra'anana (IL); Elia Bernardino Ricci, Cascinette d'Ivrea (IT)

(73) Assignee: ADB International Group Inc., San Antonio, TX (US)

(*) Notice: Subject to any disclaimer, the term of this patent is extended or adjusted under 35 U.S.C. 154(b) by 708 days.

(21) Appl. No.: 12/477,944

(22) Filed: Jun. 4, 2009

(65) Prior Publication Data

US 2010/0131031 A1 May 27, 2010

Related U.S. Application Data

(60) Provisional application No. 61/118,451, filed on Nov. 27, 2008.

(51) Int. Cl.
*A61N 1/00* (2006.01)
*A61B 5/05* (2006.01)
*A61B 5/04* (2006.01)
*A61N 1/32* (2006.01)
*A61B 5/00* (2006.01)
*A61N 1/36* (2006.01)

(52) U.S. Cl.
CPC . *A61B 5/04* (2013.01); *A61N 1/326* (2013.01); *A61B 5/7257* (2013.01); *A61N 1/36014* (2013.01)

USPC .............................................. 607/50; 600/407

(58) Field of Classification Search
USPC ........................ 607/50–52, 62; 600/300–595
See application file for complete search history.

(56) References Cited

U.S. PATENT DOCUMENTS

| | | | | |
|---|---|---|---|---|
| 4,754,763 A | * | 7/1988 | Doemland | 600/552 |
| 5,309,898 A | * | 5/1994 | Kaufman et al. | 601/2 |
| 5,368,044 A | * | 11/1994 | Cain et al. | 600/552 |
| 6,061,597 A | * | 5/2000 | Rieman et al. | 607/51 |
| 6,213,934 B1 | * | 4/2001 | Bianco et al. | 600/14 |
| 7,184,824 B2 | | 2/2007 | Hashimshony | |
| 7,361,136 B2 | * | 4/2008 | Parker | 600/14 |
| 2002/0019023 A1 | * | 2/2002 | Dasseux et al. | 435/40 |
| 2006/0270942 A1 | | 11/2006 | McAdams | |
| 2007/0179562 A1 | * | 8/2007 | Nycz | 607/51 |
| 2010/0030058 A1 | * | 2/2010 | Mammone et al. | 600/407 |

* cited by examiner

*Primary Examiner* — Catherine Voorhees
(74) *Attorney, Agent, or Firm* — Roach Brown McCarthy & Gruber, P.C.; Kevin D. McCarthy

(57) ABSTRACT

Described herein are electrical markers, specifically alternate current (AC) signals whose appearance in patients with wounds, specifically chronic wounds, correlates to the prognosis of the wounds. Related methods that can be used for diagnosis and treatment of wounds are disclosed. Also described herein are methods that can be used to identify electrical signals of wounds.

9 Claims, 16 Drawing Sheets

---

13-1 Detecting and recording a first electrical signal in and around an area of the target tissue and a second electrical signal in and around contralateral tissue.

13-2 Transforming the first and second electrical signals into a voltage versus frequency spectra using a Fast Furier Transform (FFT) algorithm.

13-3 Comparing a graph of the resultant FFT level of the first electrical signal to an FFT level of the second electrical signal and at least one graph of a baseline FFT level of wounds in a worsening state without infection.

13-4 Determining the presences of infection in the target tissue based on said comparison.

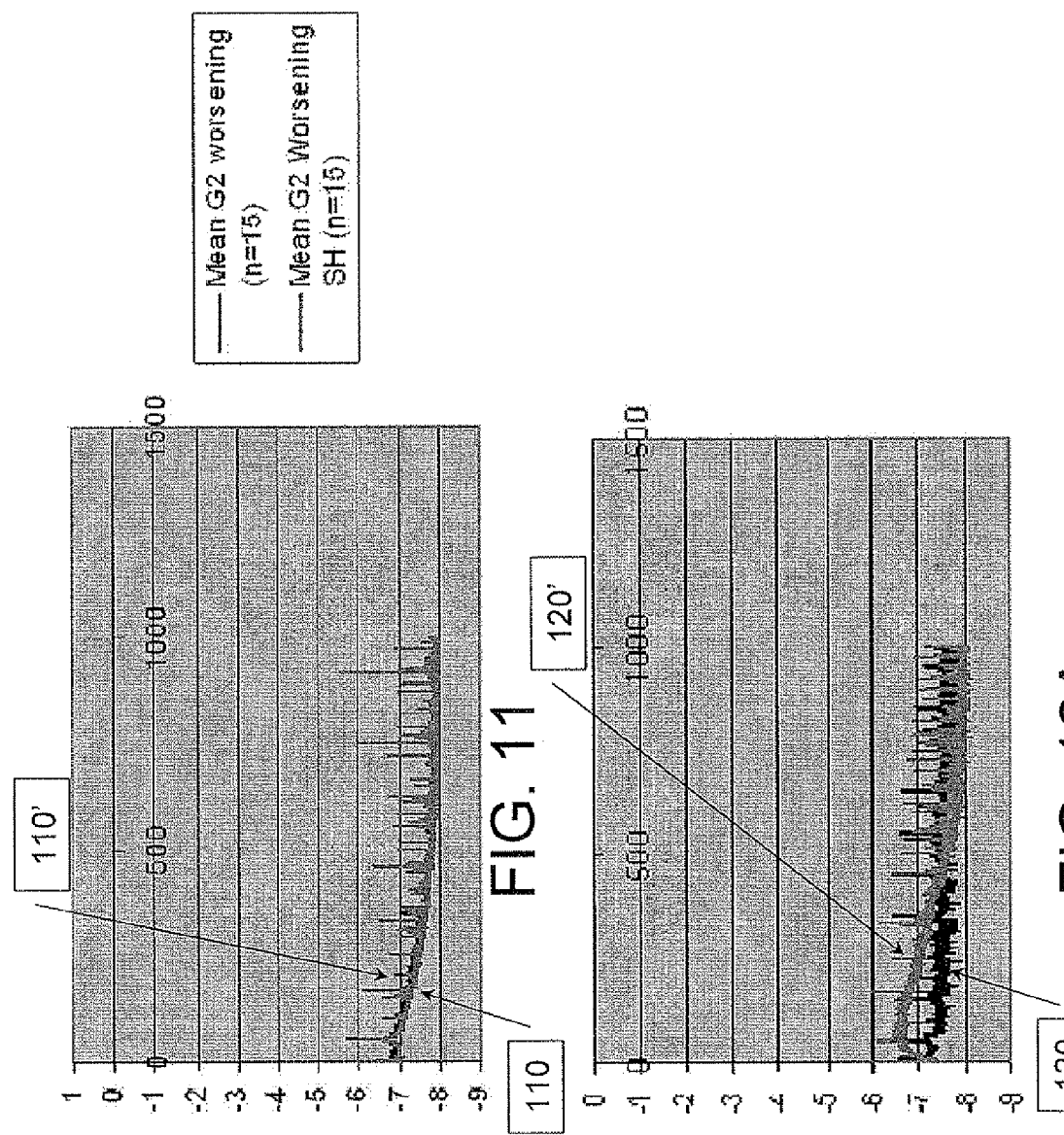

13-1 Detecting and recording a first electrical signal in and around an area of the target tissue and a second electrical signal in and around contralateral tissue.

13-2 Transforming the first and second electrical signals into a voltage versus frequency spectra using a Fast Furier Transform (FFT) algorithm.

13-3 Comparing a graph of the resultant FFT level of the first electrical signal to an FFT level of the second electrical signal and at least one graph of a baseline FFT level of wounds in a worsening state without infection.

13-4 Determining the presences of infection in the target tissue based on said comparison.

FIG. 13

14-1 Detecting and recording an electrical signal in and around an area of the target tissue, the electrical signal being a stochastic signal.

14-2 Transforming the stochastic signal into a voltage versus frequency spectra using a Fast Fourier Transform (FFT) algorithm.

14-3 Comparing a graph of a resultant FFT level of the target tissue to at least one graph of a baseline FFT level.

14-4 Determining a current state of the target tissue based on said comparison.

FIG. 14

15-1 Detecting and recording a first electrical signal in and around an area of the target tissue a second electrical signal in and around contralateral tissue, the first and the second electrical signals being a stochastic

15-2 Transforming the first and the second electrical signals into a voltage versus frequency spectra using a Fast Fourier Transform (FFT) algorithm.

15-3 Comparing a graph of a resultant FFT level of the first electrical signal to at least one graph of a baseline FFT level and an FFT level of the first electrical signal.

15-4 Determining a prognosis of the target tissue based on the comparison.

FIG. 15

16-1 Detecting and recording an electrical signal in and around an area of the target tissue, said electrical signal being a stochastic signal.

16-2 Transforming said stochastic signal into a voltage versus frequency spectra using a Fast Fourier Transform (FFT) algorithm.

16-3 Comparing a graph of a resultant FFT level of the target tissue to FFT level referenced markers.

16-4 Determining a current state of the target tissue based on said comparison.

FIG. 16

METHODS OF DIAGNOSIS AND TREATMENT OF WOUNDS, METHODS OF SCREENING FOR ELECTRICAL MARKERS FOR WOUNDS PROGNOSIS IN PATIENTS

This application claims priority from U.S. Provisional Patent Application No. 61/118,451 filed 27 Nov. 2008.

FIELD AND BACKGROUND OF THE INVENTION

The present invention relates to a method for diagnosing the prognosis of damaged animal tissues, including human tissue by detection of an electric current flow through the tissue. The invention relates to a method and procedure for measuring, recording and analyzing the electrical field in and around areas of a living body and in particular the method identifies and defines a discrete electrical profile of a wound during a healing, worsening or stopped condition.

Electrophysiology is the science and branch of physiology that delves into the flow of ions in biological tissues, the electrical recording techniques which enable the measurement of this flow and their related potential changes. One system for such a flow of ions is the Power Lab System by ADInstruments headquartered in Sydney, Australia.

Clinical applications of extracellular recording include among others, the electroencephalogram and the electrocardiogram. To understand these biomedical signals, it is necessary to understand signal types, properties and statistics.

Deterministic signals are exactly predictable for the time span of interest. Deterministic signals can be described by mathematical models. Stochastic or random signals are those signals whose value has some element of chance associated with it, therefore it cannot be predicted exactly. Consequently, statistical properties and probabilities must be used to describe stochastic signals. In practice, biological signals often have both deterministic and stochastic components.

Regarding signal amplitude statistics, a number of statistics may be used as a measure of the location or "centre" of a random signal. These include,

- The mean, which is the average amplitude of the signal over time.
- The median, which is the value at which half of the observations in the sample have values smaller than the median and half have values larger than the median. The median is often used as the measure of the "centre" of a signal because it is less sensitive to outliers.
- The mode, which is the most frequently occurring value of the signal.
- The maximal and minimal amplitude, which are the maximal and minimal value of the signal during a given time interval.
- The range or peak-to-peak amplitude, which is the difference between the minimum and maximum values of a signal.

Regarding continuous time signals versus discrete time signals, signals are continuous time signals when the independent variable is continuous, therefore the signals are defined for a continuum of values of the independent variable $X(t)$. An analogue signal is a continuous time signal. Discrete time signals are only defined at discrete times; the independent variable takes on only a discrete set of values $X(n)$. A digital signal is a discrete time signal.

A discrete time signal may represent a phenomenon for which the independent variable is inherently discrete (e.g., amount of calories per day on a diet). On the other hand, a discrete signal may represent successive samples of an underlying phenomenon for which the independent variable is continuous (e.g., a visual image captured by a digital camera is made of individual pixels that can assume different colors).

There are quantitative methods to measure the frequency and amplitude of a waveform. One of the most well known is called spectral analysis: any waveform can be mathematically decomposed in a sum of different waveforms. This is what the so-called Fourier analysis does; it decomposes the waveform in different components and measures the amplitude (power) of each frequency component. What is plotted is a graph of power (amplitude) vs. frequency.

Whereas research on direct current (DC) activity in wound healing and tissue remodeling has a long history, electric fields of alternating current (AC) with specific frequencies have been much less studied.

Specific frequencies have been detected in various biological pathways known to be associated with wound healing such as pain, cell metabolism inter-cellular communication and bone growth. However, due to the absence of suitable measurement tools, there has been no definitive proof of involvement of AC with defined frequency spectra in wounds.

Further, to date no diagnostic method based on a discrete electrical profile that provides a prognosis for wound healing has been ventured in the medical filed.

There is therefore a need for a diagnostic method that identifies and defines a discrete electrical profile of a wound during a healing, worsening or stopped condition so as to provide a prognosis for such wounds. It would be beneficial if the method is linked to an appropriate electrical pulse transmission device in order to monitor and adjust the electrical therapy applied to damaged tissue based on the measured electrical field of the relevant tissues of the body.

SUMMARY OF THE INVENTION

The present invention is a diagnostic method that identifies and defines a discrete electrical profile of a wound during a healing, worsening or stopped condition so as to provide a prognosis for such wounds.

According to the teachings of the present invention there is provided, 1.

A method of detecting the current state of living human and animal target tissue, the method comprising: (a) detecting and recording an electrical signal in and around an area of the target tissue, the electrical signal being a stochastic signal; (b) transforming the stochastic signal into a voltage versus frequency spectra using a Fast Furier Transform (FFT) algorithm; (c) comparing a graph of a resultant FFT level of the target tissue to at least one graph of a baseline FET level; and (d) determining a current state of the target tissue based on the comparison.

According to a further teaching of the present invention, the detecting and recording is implemented as detecting and recording an alternating current (AC) signal and displaying the alternating current (AC) signal as voltage over time.

According to a further teaching of the present invention, the FFT level is implemented as an electrical frequency spectra from 0 to 5000 Hz.

According to a further teaching of the present invention, the FFT level is implemented as an electrical frequency spectra from 0 and 3000 Hz.

According to a further teaching of the present invention, the target tissue is an area of injury in a patient.

According to a further teaching of the present invention, the baseline is implemented as the FFT levels for healthy non-injured subjects.

According to a further teaching of the present invention, the baseline is implemented as an FFT level for normal healthy tissue and an increase in the FFT level of the target tissue relative to the baseline FFT level is indicative of wound conditions.

According to a further teaching of the present invention, the current state of the target tissue includes one from a list that includes worsening condition, healing condition and stopped condition.

According to a further teaching of the present invention, the FFT level of the target tissue is implemented so as to enable differentiation of wounds that are in a worsening condition due to infection from wounds that are in a healing state and from wounds that are in a stopped state.

According to a further teaching of the present invention, there is also provided comparing the graph of a resultant FFT level of the target tissue to FFT level referenced markers.

According to a further teaching of the present invention, the FFT level reference markers are implemented so as to indicate wounds in a worsening state, a healing state and a stopped state According to a further teaching of the present invention, the FFT level reference markers are implemented as mean FFT level profiles detected in healthy subjects, patients with chronic wounds diagnosed as worsening, patients with chronic wounds diagnosed as healing and patients with chronic wounds diagnosed as stopped.

According to a further teaching of the present invention, there is also provided: (a) providing data regarding the current state of the target tissue to a devise for transmitting an alternate current to the target tissue; and (b) transmitting an alternate current signal to the target tissue wherein a specific frequency spectra is determined by the data.

According to a further teaching of the present invention, the determining further includes determining a prognosis for the target tissue.

There is also provided according to the teachings of the present invention, a method for determining a prognosis for wounds in a living human and animal target tissue, the method comprising: (a) detecting and recording a first electrical signal in and around an area of the target tissue a second electrical signal in and around contralateral tissue, the first and the second electrical signals being a stochastic signals; (b) transforming the first and the second electrical signals into a voltage versus frequency spectra using a Fast Fourier Transform (FFT) algorithm; (c) comparing a graph of a resultant FFT level of the first electrical signal to at least one graph of a baseline FFT level and an FFT level of the second electrical signal; and (d) determining a prognosis of the target tissue based on the comparison.

There is also provided according to the teachings of the present invention, a method of a prognosis for wounds in living human and animal target tissue, the method comprising: (a) detecting and recording an electrical signal in and around an area of the target tissue, the electrical signal being a stochastic signal; (b) transforming the stochastic signal into a voltage versus frequency spectra using a Fast Fourier Transform (FFT) algorithm; (c) comparing a graph of a resultant FFT level of the target tissue to at least one FFT level referenced marker; and (d) determining a current state of the target tissue based on the comparison.

According to a further teaching of the present invention, the FFT level reference markers are implemented so as to indicate wounds in a worsening state, a healing state and a stopped state According to a further teaching of the present invention, the FFT level reference markers are implemented as mean FFT level profiles detected in healthy subjects, patients with chronic wounds diagnosed as worsening, patients with chronic wounds diagnosed as healing and patients with chronic wounds diagnosed as stopped.

There is also provided according to the teachings of the present invention, an electrical stimulator system for providing treatment to a target tissue, the electrical stimulator system comprising: (a) a first component configured for detecting and recording an electrical signal in and around an area of the target tissue, the electrical signal being a stochastic signal, the device further configured to transform the stochastic signal into a voltage versus frequency spectra using a Fast Fourier Transform (FFT) algorithm, use a resultant FFT level to generate data regarding a current state of the target tissue and transmit the data; (b) a second component configured to deliver an electrical current to the target tissue, the devise configured to receive the data from the first component, characteristics of the electrical current being determined by the data.

According to a further teaching of the present invention, the characteristics include a specific frequency spectra.

According to a further teaching of the present invention, the electrical current delivered to the target tissue is an alternate current signal.

There is also provided according to the teachings of the present invention, a method of determining the presence of infection in a worsening wound in living human and animal tissue, the method comprising: (a) detecting and recording a first electrical signal in and around an area of the target tissue a second electrical signal in and around contralateral tissue, the first and the second electrical signals being a stochastic signals; (b) transforming the first and the second electrical signals into a voltage versus frequency spectra using a Fast Fourier Transform (FFT) algorithm, (c) comparing a graph of a resultant FFT level of the first electrical signal to an FFT level of the second electrical signal and at least one graph of a baseline FFT level of wounds in a worsening state without infection; and (d) determining a presences of infection in the target tissue based on the comparison.

BRIEF DESCRIPTION OF THE DRAWINGS

The invention is herein described, by way of example only, with reference to the accompanying drawings, wherein:

FIG. 11 is a graph the FFT level around a chronic wound and the FFT level for the contralateral non-injured tissue for the group of subjects having wounds in a worsening state without injection;

FIG. 12A-12E are graphs the FFT level around a chronic wound and the FFT level for the contralateral non-injured tissue for five individual subjects having wounds in a worsening state due to infection;

FIG. 13 is a flowchart of a method, according to the teachings of the present invention, of determining if a worsening wound in target tissue is infected;

FIG. 14 is a flowchart of a method, according to the teachings of the present invention, for detecting the current state of living human and animal target tissue;

FIG. 15 is a flowchart of a first method, according to the teachings of the present invention, for determining a prognosis for wounds in living human and animal target tissue; and FIG. 16 is a flowchart of a second method, according to the teachings of the present invention, for determining a prognosis for wounds in living human and animal target tissue.

DESCRIPTION OF THE PREFERRED EMBODIMENTS

Figure 1:
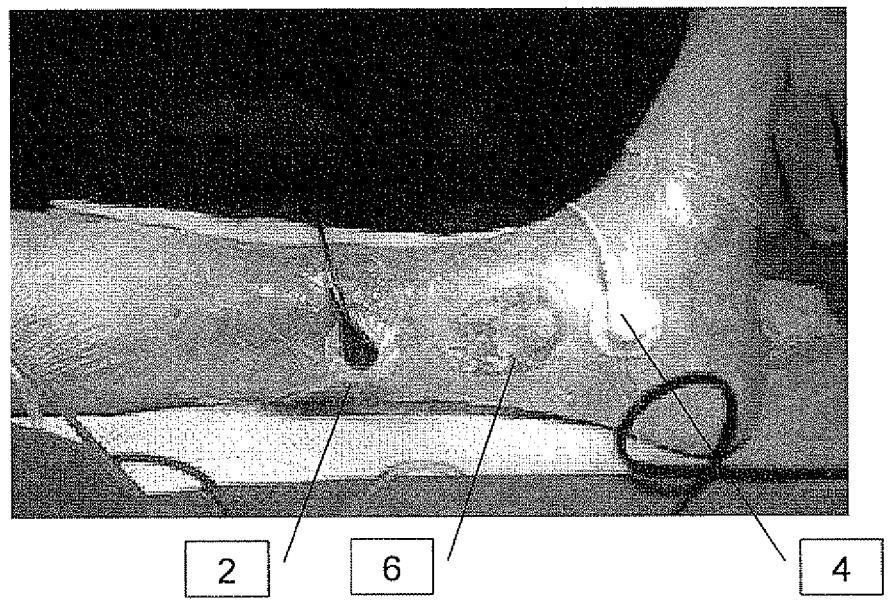
FIG. 1 illustrates placement of electrodes near a wound.

The present invention relates to a diagnostic method that identifies and defines a discrete electrical profile of a wound during a healing, worsening or stopped condition so as to provide a prognosis for such wounds.

The principles and operation of a diagnostic method that identifies and defines a discrete electrical profile of a wound so as to provide a prognosis for such wounds according to the present invention may be better understood with reference to the drawings and the accompanying description.

By way of introduction, electrical flow in the body plays a major role in many physiological and pathophysiological conditions. During tissue injury, direct electrical current known as "the current of injury" is triggered (or generated) around the wound. However, alternating current characterized by specific frequencies, is mainly attributed in medicine to the action or injury of nerves but with much less focus on wounds. Research by the present inventors has identified in humans the presence of discrete alternating current signals that are specific to patients with chronic wounds in comparison to healthy subjects. They conducted simultaneous alternating current measurements on the same patients at their injured where there is an existing chronic wound and on the contralateral non injured limb. They then activated an algorithm to transform these stochastic signals to frequency spectra and found that the same signal pattern exists around the wound and throughout the patient's body. These discrete microcurrent signals display unique frequency profiles within the range of 0.5-500 Hz. Furthermore, electrical recordings of chronic wounds taken during an acute injury state induced by their debridement revealed an instantaneous stochastic signal with a frequency pattern exceeding 1000 Hz, a signal that was triggered simultaneously around the acute wound and on the contralateral healthy limb of the same patient. Their findings emphasize the possible systemic attribute of alternating current signaling in wound healing. They indicate that this electrical signaling may be linked to a possible "cross talk" between the central nervous system and wounds. They suggest that electrical frequencies should be considered as a relevant marker to study wound healing.

Whereas research on direct current (DC) in wound healing and tissue remodeling has a long history, electric fields of alternating current (AC) with specific frequencies have been much less studied.

Specific frequencies have been detected in various biological pathways known to be associated with wound healing such as pain, cell metabolism, inter-cellular communication and bone growth. However, due to the absence of suitable measurement tools, there has been no definitive proof of involvement of AC with defined frequency spectra in wounds.

In their research the present inventors aimed to elucidate whether oscillating characteristics of specific frequency components exist around injured tissues in humans. They wished to identify discrete AC cues linked to a specific spectrum of frequencies adjacent to chronic non-healing wounds and to determine whether these AC cues could be detected during acute injury.

For this objective, on the same group of patients we conducted electrical recordings on both injured and on non-injured tissue, with the measurements on non-injured tissue used for control.

For electrical recordings we affixed two electrodes on both proximal and distal sides across the medial axis of the injured skin (FIGS. 1 and 2) and signals were measured against the third ground electrode (not shown). In order to amplify the specificities of the recorded AC signals a Fast Fourier Transform (FFT) algorithm was used. By this signal processing approach they were able to profile discrete signals with significant differences in amplitude (voltage) and/or frequency within a filter set at 0.5 to 1000 Hz.

To establish the baseline levels of our electrical measurements, we recruited healthy subjects (no wounds) and the graph of their mean FFT levels served as the minimal amplitude levels i.e., baseline.

To test the role of endogenous electrical frequencies in damaged tissue, we first focused on patients with chronic wounds as the target population. Chronic wounds are trapped in a non-advancing phase of healing and are unable to progress through the sequential stages of tissue repair. Compared to acute wounds, studies have shown that human chronic wounds differ in their biochemical, molecular and mechanistic characteristics such as reduced levels of metalloproteinase inhibitors and diminished growth factor activity. Therefore, unlike acute wounds that are dynamically changed in time, chronic wounds may be considered relatively stable and thus could provide an example of the profile of their mean electric fields. The mean electrical measurements around chronic wounds exhibited significantly higher amplitude (voltage) above the baseline measurements in healthy subjects. These stochastic signals were characterized by mean electrical frequency spectra within the range of 0.5 to 500 Hz. The mean maximum voltage (Vmax) of this signal was found in the range of 0.5 to 50 Hz (a frequency range considered as environmental electrical radiation). The signal reduced exponentially to its minimal voltage (Vmin) of about 10 nV which was detected around 500 Hz. Due to the absence of such signals in the baseline group of healthy subjects we confirmed that this discrete signal is specific to chronic wounds.

In order to confirm that the specific signal detected around wounds is specific to the wound site, similar measurement on the contralateral healthy limb of the same chronic wound patients. Intriguingly, it was found in the same patients that the stochastic waveform that exists around wounds, overlapped with same electrical frequency spectra and amplitude of the signals recorded on the contralateral non-injured organ. It is therefore deduced that the discrete stochastic signals found in patients with chronic wounds could also serve as a systemic parameter in the body. These statistically significant results (FIG. 4) highlight the possibility that chronic wounds may be studied as local tissue damage with systemic attributes.

To investigate the origin of the local and systemic signals found around chronic wounds, it was necessary to find how this type of stochastic signal is produced in the body. Although studies on "the current of acute injury" have claimed that this is a type of DC signal, we speculated that the stochastic signals identified here in chronic wounds may originate from prior AC signals produced during the acute stages of these chronic wounds. To address this hypothesis, patients with diagnosed chronic wounds that were allocated to a surgical debridement procedure were recruited. The clinical rationale of chronic wound debridement is to release the chronic wound from its arrested state by removing nonviable tissue, bacteria, and other inhibitory factors, effectively converting it into an acute wound that can undergo healing more effectively. Considering the research study prospective, the debridement procedure provided an excellent example for evaluating the dynamics of electrical frequency pattern before and during this procedure. It should be emphasized that in these cases it was possible to simultaneously analyze the dynamics of the signals before and during acute injury on both the wound and contralateral non-injured organs. The generated signal exhibited significantly higher amplitude above the amplitude levels of the basal signal and its frequency spectra exceeded 1000 Hz much above the chronic wound signals. Furthermore, the present inventors found the intriguing result of the simultaneous increase and existence of these injury signals on both the wound and on the contralateral healthy limb of the same patients. Considering that the debridement procedures were done here with no aid of anesthesia, the findings on the instantaneously triggered signals during this acute injury indicate a possible involvement of somatosensory afferent or efferent nerves in this signaling. Furthermore, preliminary electrical recordings on anesthetized patients (blockage of sensory nerves) show that during incision i.e., in acute wounds, we detected AC signals with considerably weak amplitudes (around the baseline levels), another indication that nerves or nerve injury may be involved in the AC signaling found here during acute injury.

The existence of defined specific electrical frequencies in the central nervous system is well documented in medicine, and these are fundamental markers in the monitoring and studies of brain activity. Despite studies on pain, the role of electrical frequencies in other peripheral disorders such as tissue injury have been much less studied. The results of the research done by the present inventors clearly demonstrate the relevance of electrical frequencies in the electrophysiology of the body's periphery; the research focused on both chronic wounds and on acute injury. Under the experimental conditions, acute injury elicits AC signals with significantly higher amplitude and frequency than those detected around chronic wounds. The findings on the discrete frequency pattern triggered during the acute injury of chronic wounds, both at injured and non-injured tissue provide a new perspective on the reported DC "current of injury".

Based on the above research, the method of detecting the prognosis of wounds in a patient of the present invention was developed. The method of detecting the prognosis of wounds in a patient of the present invention includes detecting and record an electrical signal, specifically alternating current displayed as voltage during time, from the patient, wherein the electrical signal is a stochastic signal. The stochastic signal is then transformed to voltage versus frequency spectra by the Fast Fourier Transform (FFT) algorithm. The FFT graph comprises an electrical frequency spectra from 0 to 5000 Hz and more specific to 0 and 1000 Hz.

The FFT level of the wound sample is then compared to the (baseline) FFT level in a normal sample, such as a healthy subject for example. An increase in the level of the FFT relative to the normal sample is indicative of wound conditions.

Therefore, the prognostic method of the present invention can also be a prognostic scale, or a prognostic electrical scale, with a discrete FFT such that the FFT is specific to chronic wounds that enables to differentiate between wounds that are in a worsening state, wounds that are in healing state and wounds that are neither worsening nor healing but are in a stopped state.

The stochastic signal is detected by using alternating current measurements with the signal displayed as voltage during time.

The stochastic signal transformed to FFT may be displayed as voltage as a function of frequencies, such that the FFT level is defined as the area under the voltage versus frequency curve.

An alternating current probe may be used to detect the stochastic signal that is then transformed by algorithm to FFT.

It will be understood that the probe may include, but is not limited to, electrodes, anodes, and cathodes, placed around the wound. A ground reference electrode may be placed on the skin contralateral healthy limb.

The prognostic scale of the present invention may use the mean FFT of healthy subjects as the baseline value to define a wound as worsening, healing or stopped.

Alternatively and/or additionally, the prognostic scale of the present invention may use reference markers taken from healthy tissue, worsening wounds, healing wounds and stopped wounds to define a wound as worsening, healing or stopped.

The reference markers may be, by non-limiting example, the mean FFT profiles detected in healthy subjects, patients with chronic wounds diagnosed as worsening, patients with chronic wounds diagnosed as healing and patients with chronic wounds diagnosed as stopped.

It will be appreciated that the prognosis scale of the present invention may be operationally linked to a device for delivering alternating current to human tissue such that upon determination of the current status of the wound, the device transmits to the tissue an alternating current with specific frequency spectra for worsening, healing or stopped wounds.

Figure 2:
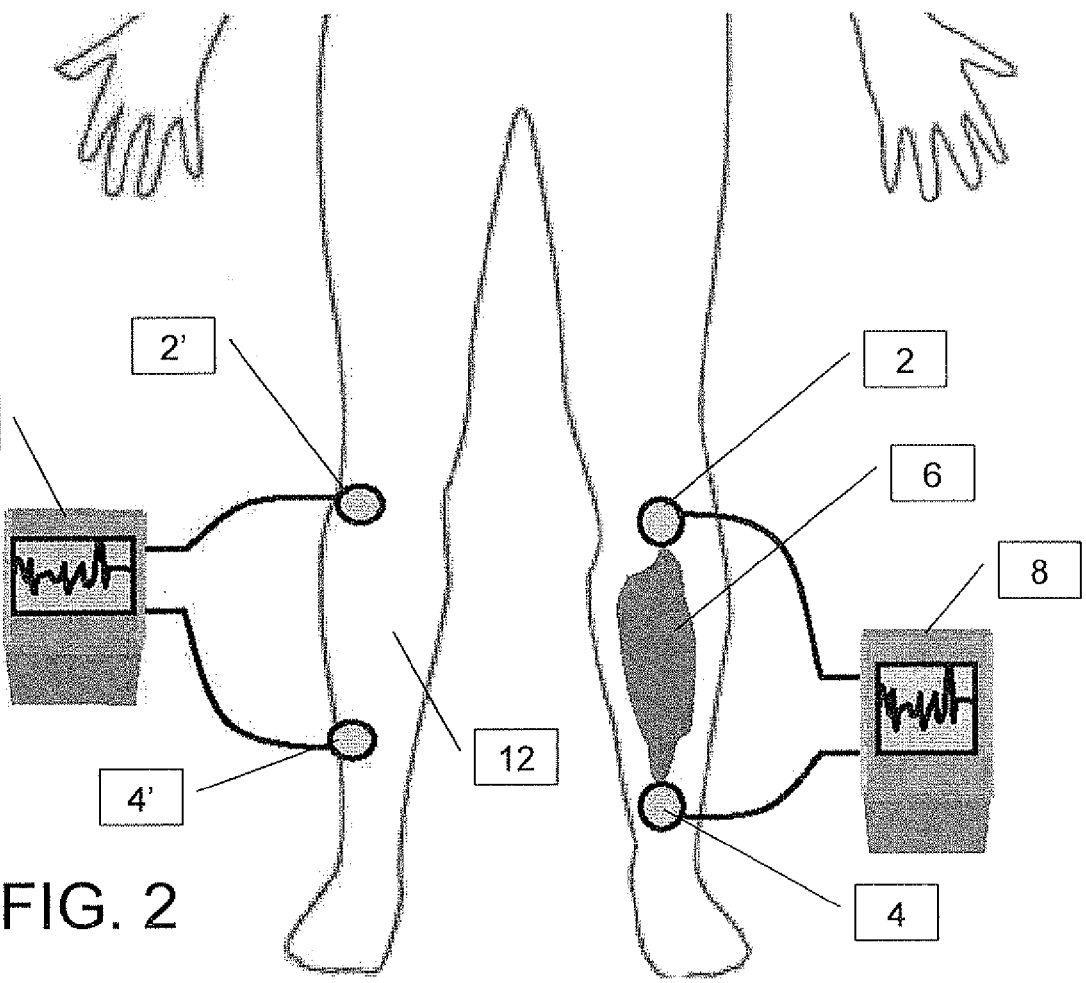
FIG. 2 illustrates the placement of electrodes near a wound and on the contralateral healthy limb.

Referring now to the drawings in more detail, FIGS. 1 and 2 illustrate the electrical recordings procedure of the present invention which affixes two electrodes 2 and 4 on both proximal and distal sides across the medial axis of the injured skin 6 and signals were measured against the third ground electrode (not shown). For simultaneous comparison two AC recording devices can be used, as seen in FIG. 2, with one device 8 placed around the wound and the other device 10 together with electrodes 2' and 4'. on the contralateral healthy limb 12 for real time comparison. It will be appreciated that device 8 may electrical stimulator system for providing treatment to a target tissue that includes a first component configured for detecting and recording an electrical signal in and around an area of the target tissue 6, transform the signal into a voltage versus frequency spectra using a Fast Fourier Transform (FFT) algorithm, use a resultant FFT level to generate data regarding a current state of the target tissue and transmit the data to a second component configured to deliver an electrical current to the target tissue 6, such that the characteristics of the electrical current delivered is determined by the data regarding a current state of the target tissue.

Figure 3A:
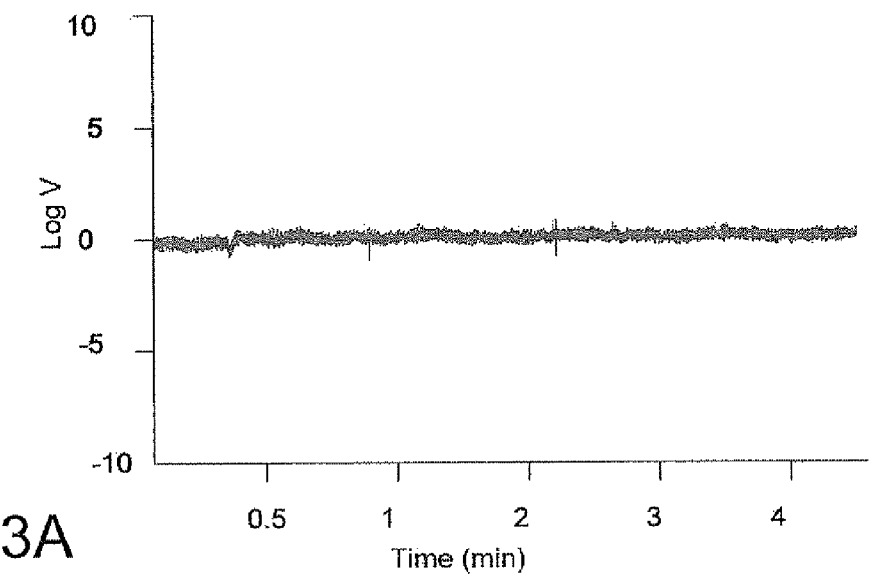
FIG. 3A is a graph of raw baseline data for a healthy subject.
Figure 3B:
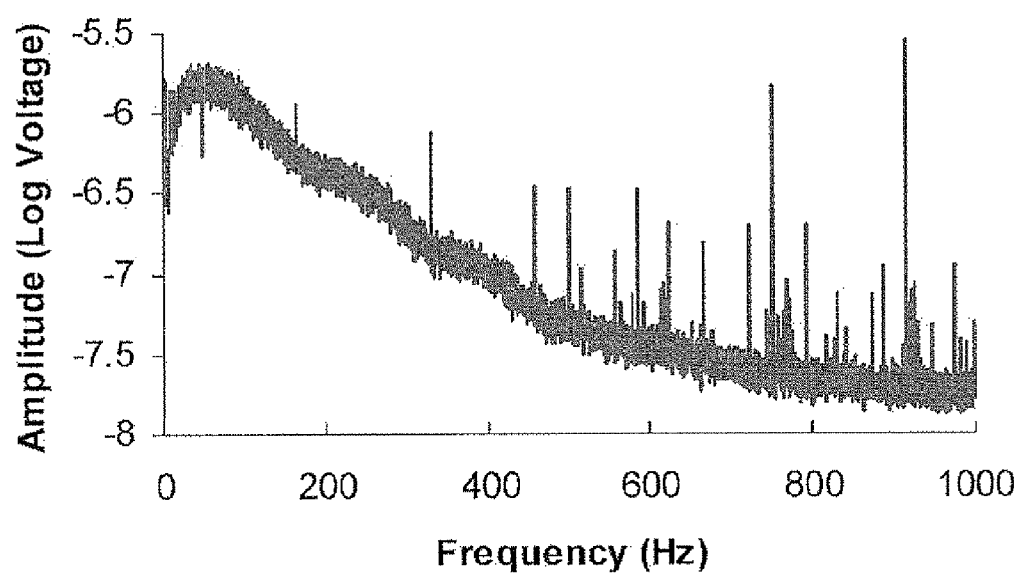
FIG. 3B is a graph of baseline data of FIG. 3A after transformation to FFT levels.
Figure 3C:
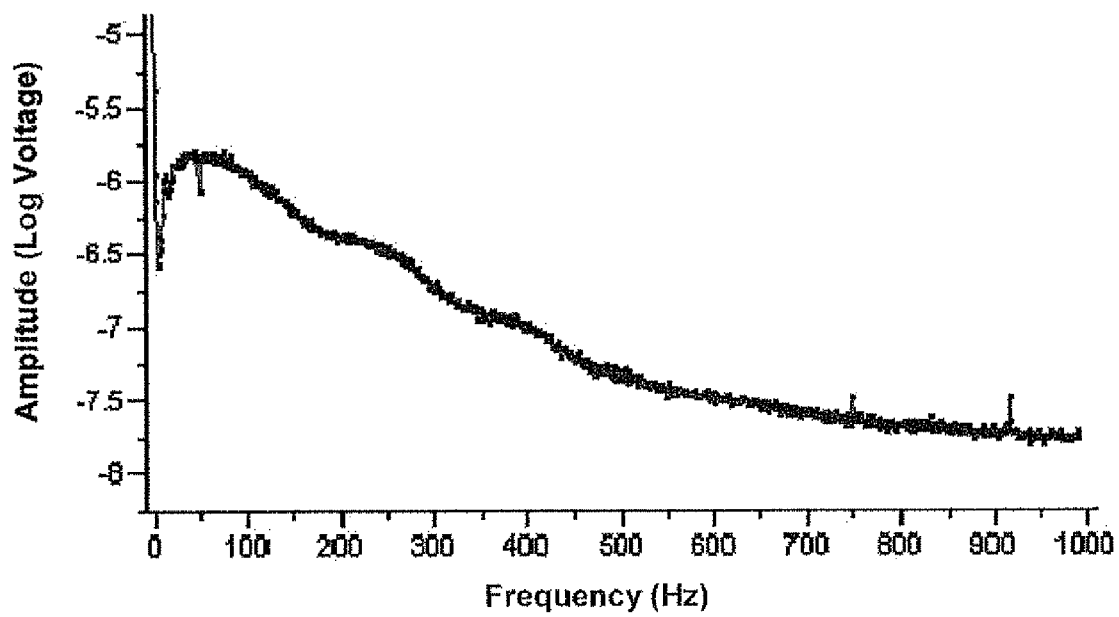
FIG. 3C is a graph of baseline data of FIG. 3B when filtered.

FIG. 3A illustrates the AC signal displayed during time (voltage against time) as a stochastic cue. In order to amplify the specificities of this signal, an algorithm of Fast Fourier Transform (FFT) is applied. This transformation enables display of the original detected signal as voltage versus frequency spectra as illustrated in FIG. 3B. This signal processing approach enables the profiling of discrete signals with significant differences in amplitude (voltage) and/or frequency within a filter set at 0.5 to 1000 Hz and up to 2000 Hz. In order to improve the signal to noise of the FFT (sampling rate of 16 per 1 second) the sampling rate is reduced to one sample per second (1 Hz) by the this an improved signal obtained with less noises as seen in FIG. 3C.

Figure 4:
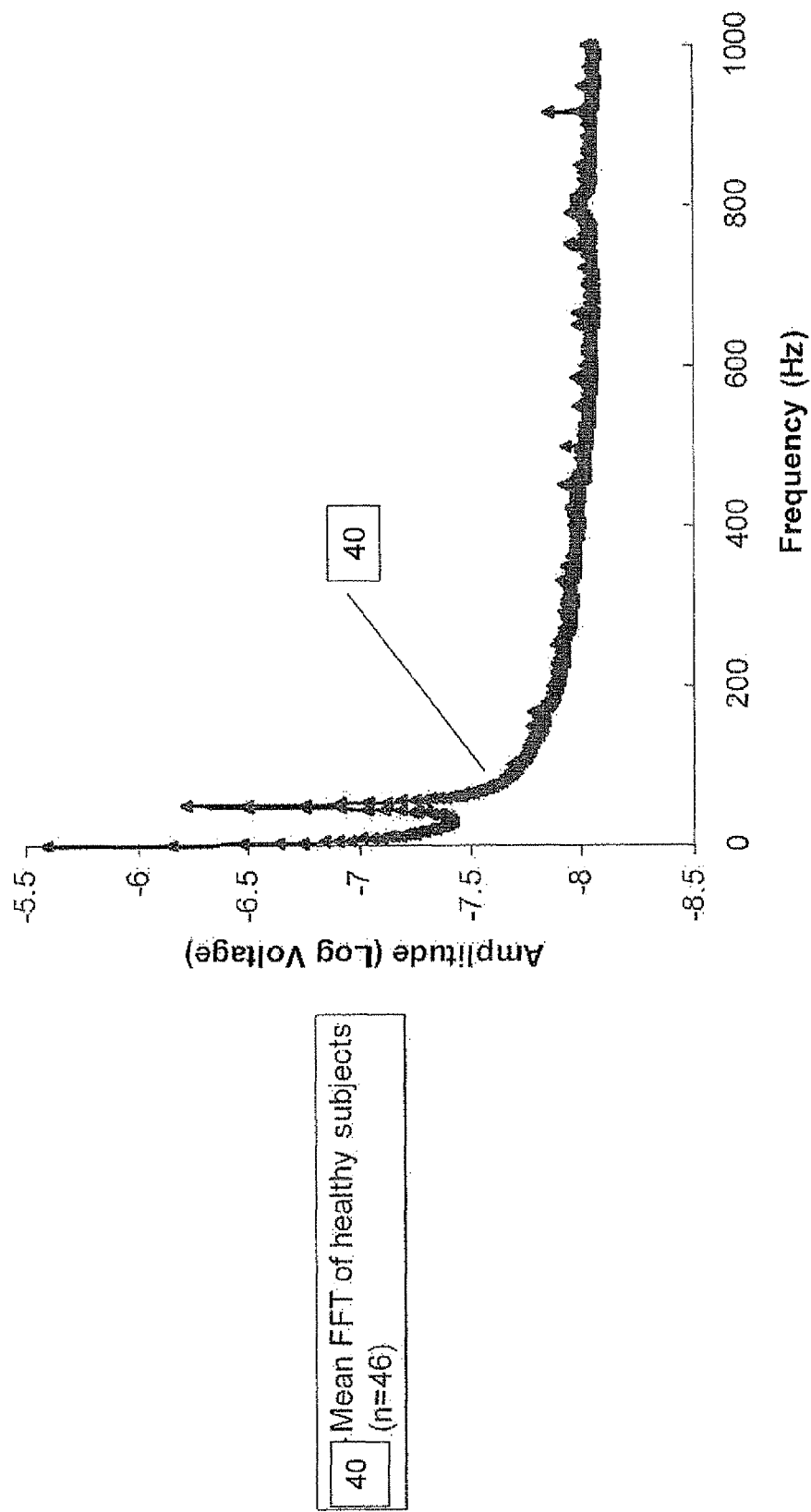
FIG. 4 is a graph of the FFT baseline for healthy subjects.

To establish the baseline levels of electrical measurements on patients, measurements conducted on healthy subjects (no wounds) and their mean FFTs served as the minimal amplitude levels i.e., baseline. FIG. 4 shows the mean frequency spectra detected on the healthy skin of healthy subjects that served as the baseline for the prognosis of wounds.

Figure 5:
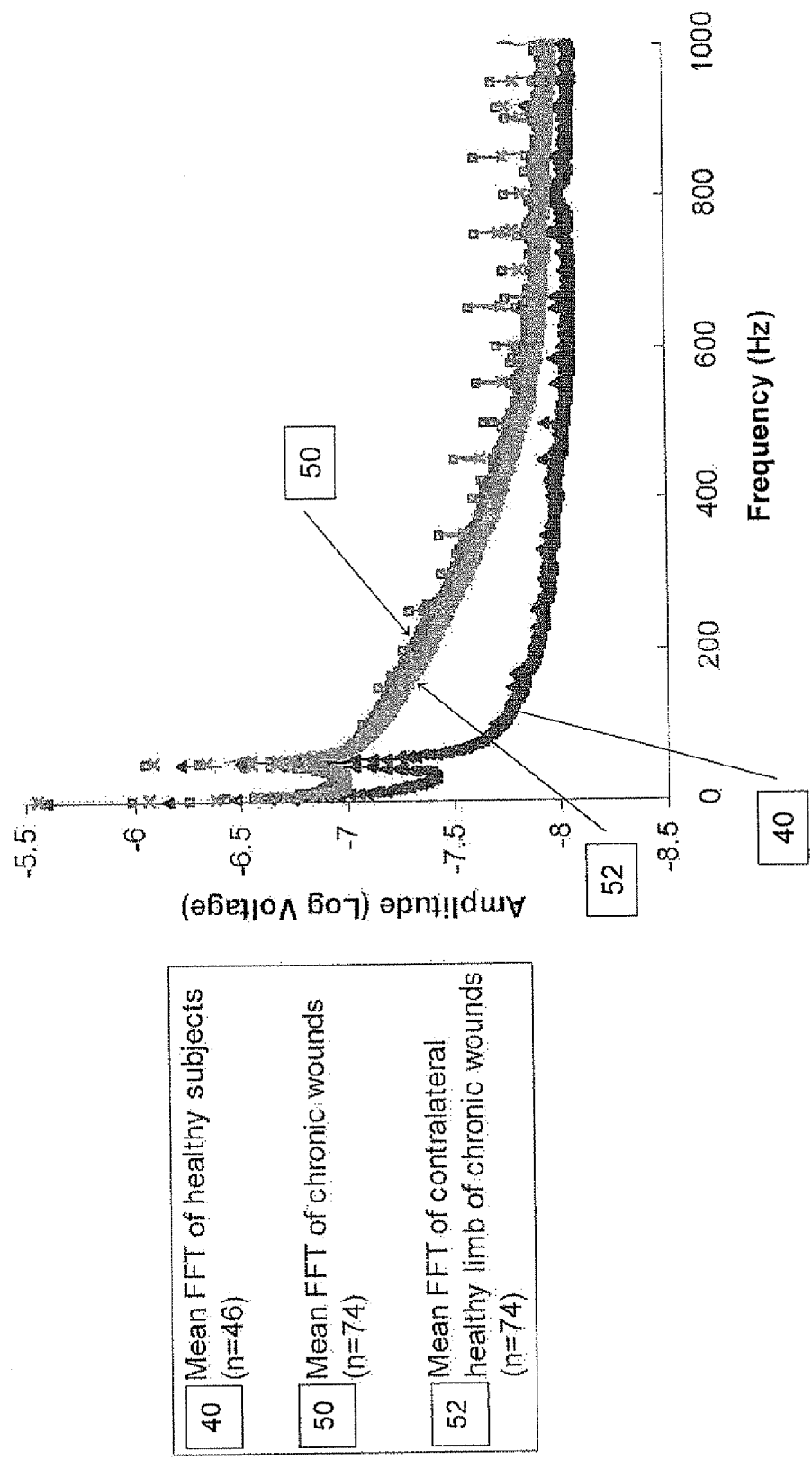
FIG. 5 is a graph of the FFT baseline for healthy subjects, the FFT level for chronic wounds and the FFT level for the contralateral non-injured tissue of the subjects with wounds.

FIG. 5 is a graph of the FFT baseline for healthy subjects 40, the FFT level for chronic wounds 50 and the FFT level for the contralateral non-injured tissue of the subjects with wounds 52. The mean electrical measurements around chronic wounds 50 exhibited significantly higher amplitude (voltage) above the baseline measurements of healthy subjects 40. These stochastic signals were characterized by mean electrical frequency spectra within the range of 0.5 to 1000 Hz. The mean maximum voltage (Vmax) of this signal was found in the range of 0.5 to 50 Hz (the frequency spike around 50 Hz is considered as environmental electrical radiation). The signal reduced exponentially to its minimal voltage (Vmin) of about 10 nV which was detected around 200 and up to 1000 Hz (in the baseline curve) and of about 20 nV within the range of 700 to 1000 Hz in the chronic wounds group. The significant higher Area Under the Curve (AUC) of the chronic wounds signals above the baseline confirmed that this discrete signal is specific to chronic wounds.

A comparable measurement was conducted on the same patient by a similar measurement procedure on the patient contralateral healthy limb. The figure shows that in the same patients the stochastic waveform which exists around wounds, overlapped with same electrical frequency spectra and amplitude on the contralateral non-injured organ 52. This means that the discrete stochastic signals found in patients with chronic wounds could also serve as a systemic marker in the body.

Figure 6:
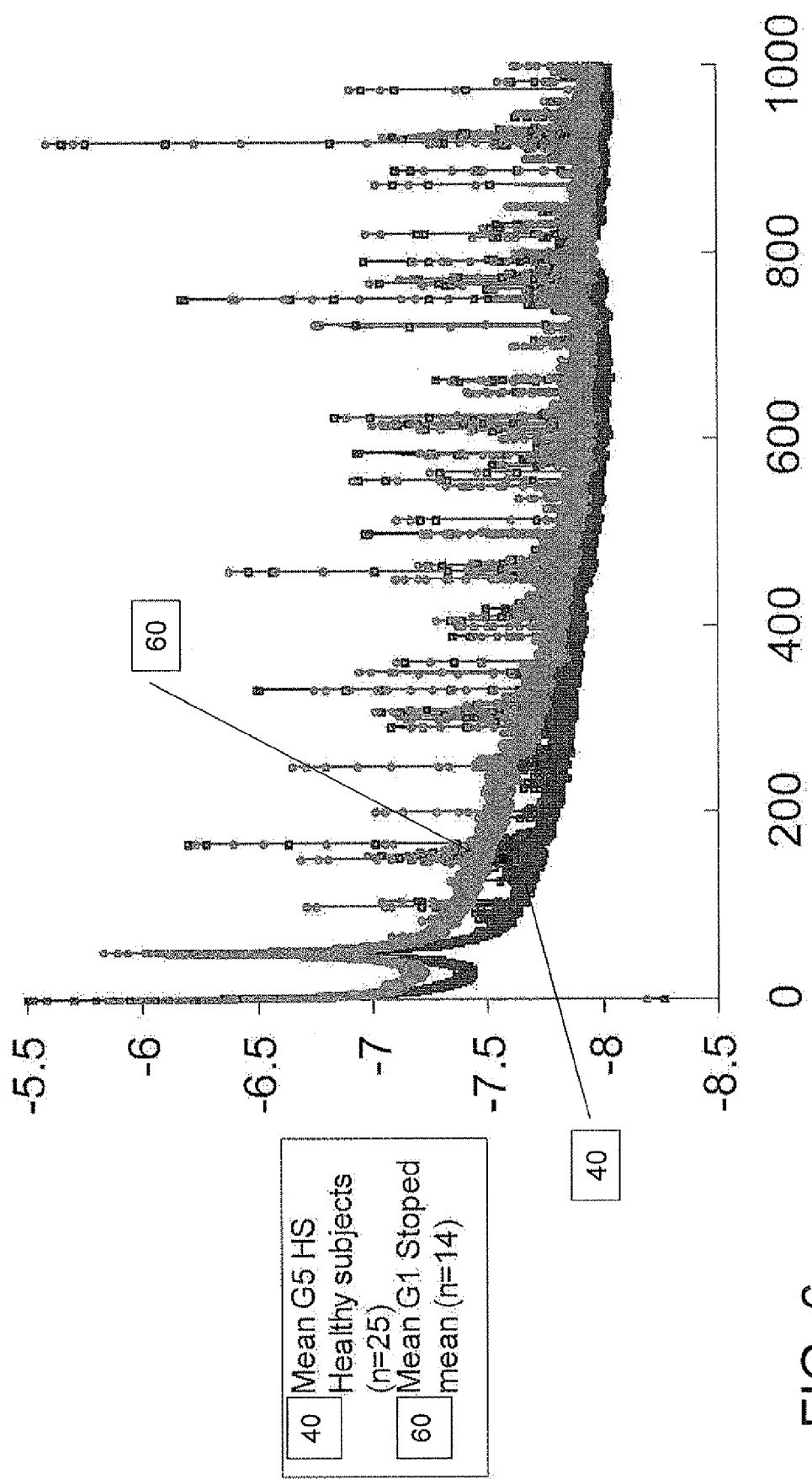
FIG. 6 is a graph of the FFT baseline for healthy subjects and the FFT level for wounds in a stopped state.

FIG. 6 shows the significant higher amplitudes exhibited by the mean FFT levels of the group of patients having wounds in stopped condition 60 above the mean FFT levels of healthy subjects 40.

Figure 7:
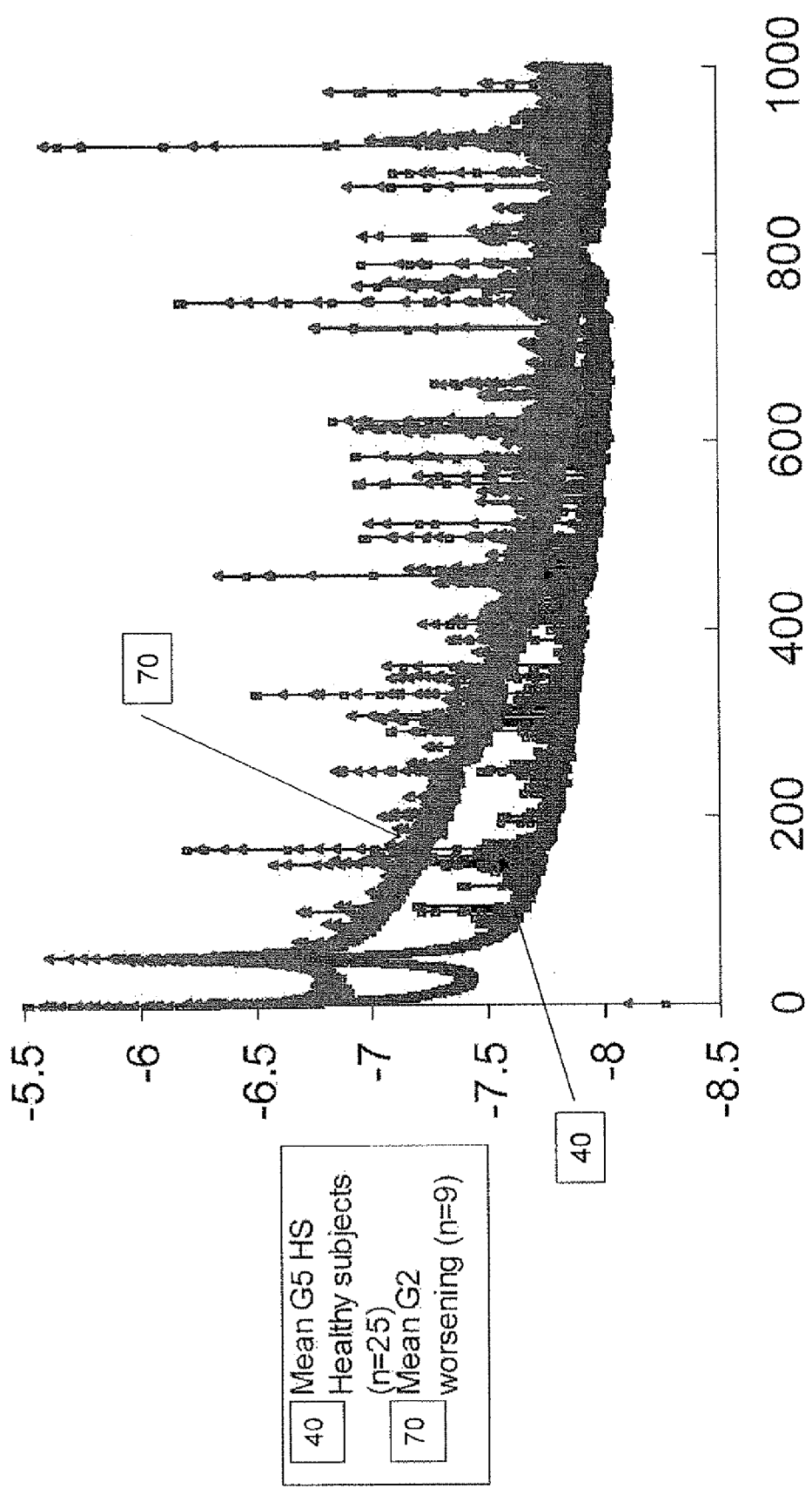
FIG. 7 is a graph of the FFT baseline for healthy subjects and the FFT level for wounds in a worsening state.

FIG. 7 shows the significant higher amplitudes exhibited by the mean FFT levels of the group of patients having wounds in worsening condition 70 above the mean FFT levels of healthy subjects 40.

Figure 8:
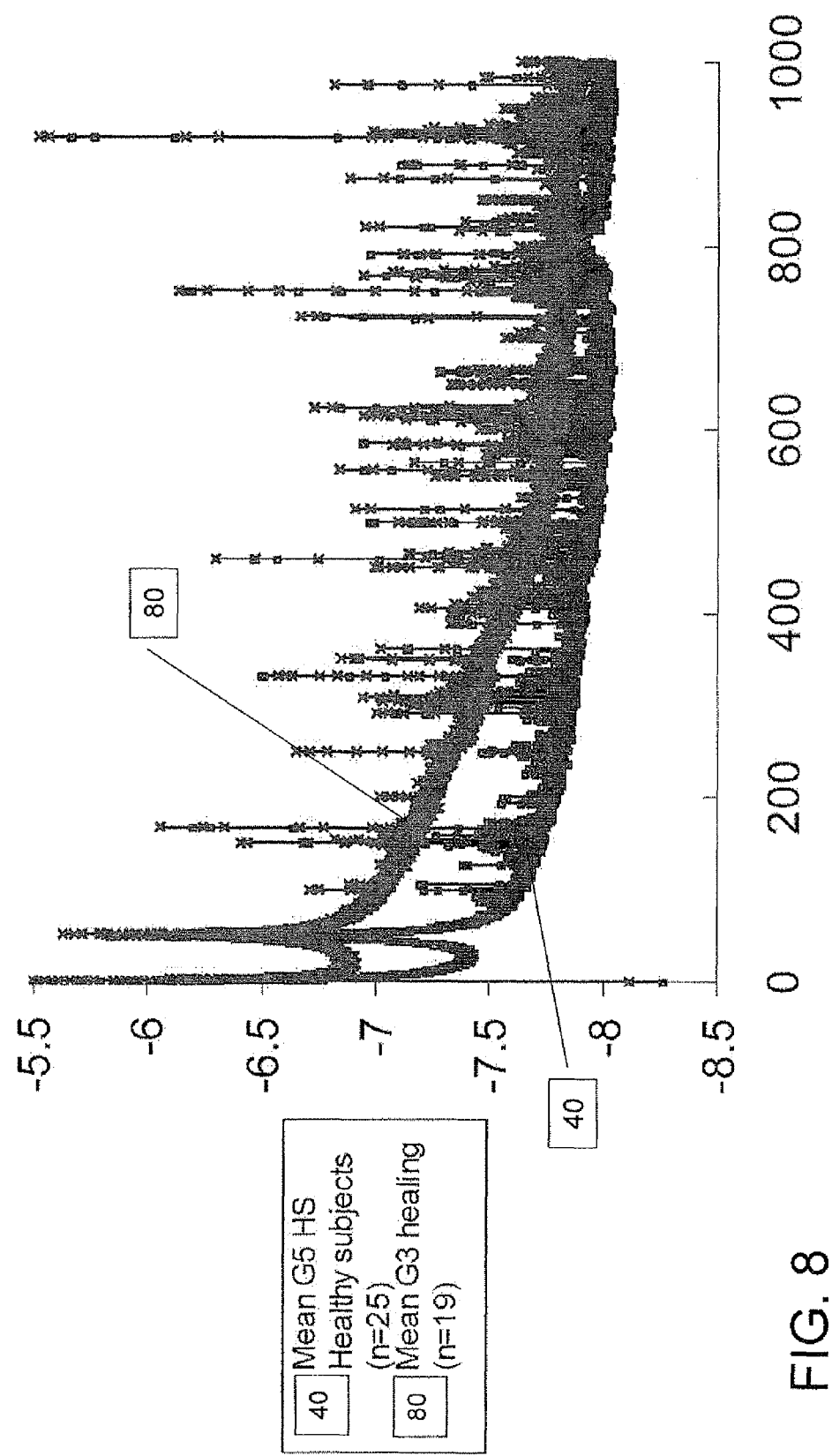
FIG. 8 is a graph of the FFT baseline for healthy subjects and the FFT level for wounds in a healing state.

FIG. 8 shows the significant higher amplitudes exhibited by the mean FFT levels of the group of patients having wounds in healing condition 80 above the mean FFT levels of healthy subjects 40.

Figure 9:
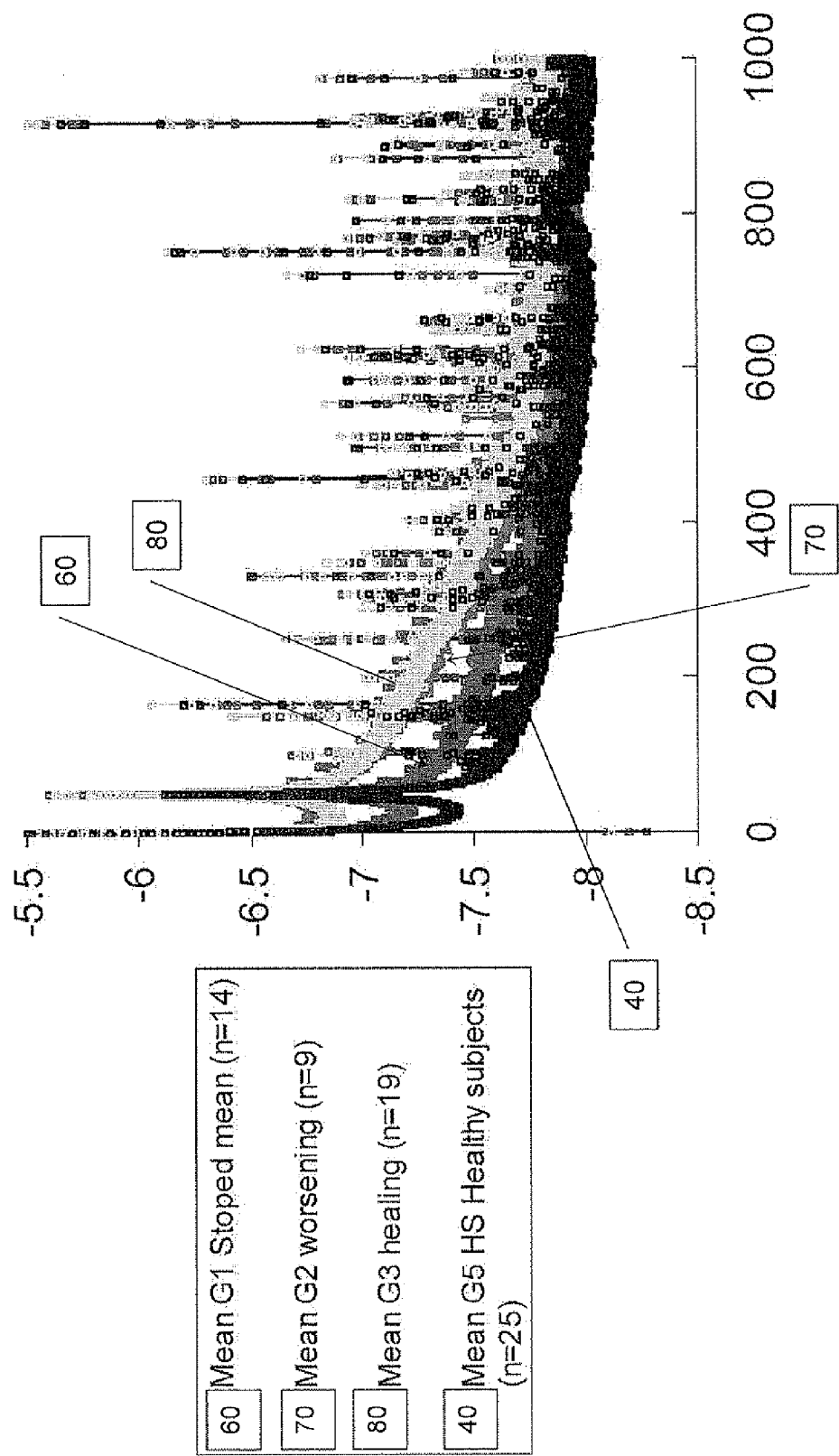
FIG. 9 is a graph of the FFT baseline for healthy subjects, the FFT level for wounds in a stopped state, the FFT level for wounds in a worsening state and the FFT level for wounds in a healing state.

FIG. 9. shows the comparison between the graphs of FIGS. 6-8. Specifically, the FFT levels for healthy subject compared to the FFT levels of patients with chronic wounds heaving in a stopped state 60, worsening state 70 or healing state 80. The figure shows that significant differences are found between the three prognostic levels of wounds. The worsening and healing are above stopped and all three are higher that the baseline of healthy subjects 40.

Figure 10:
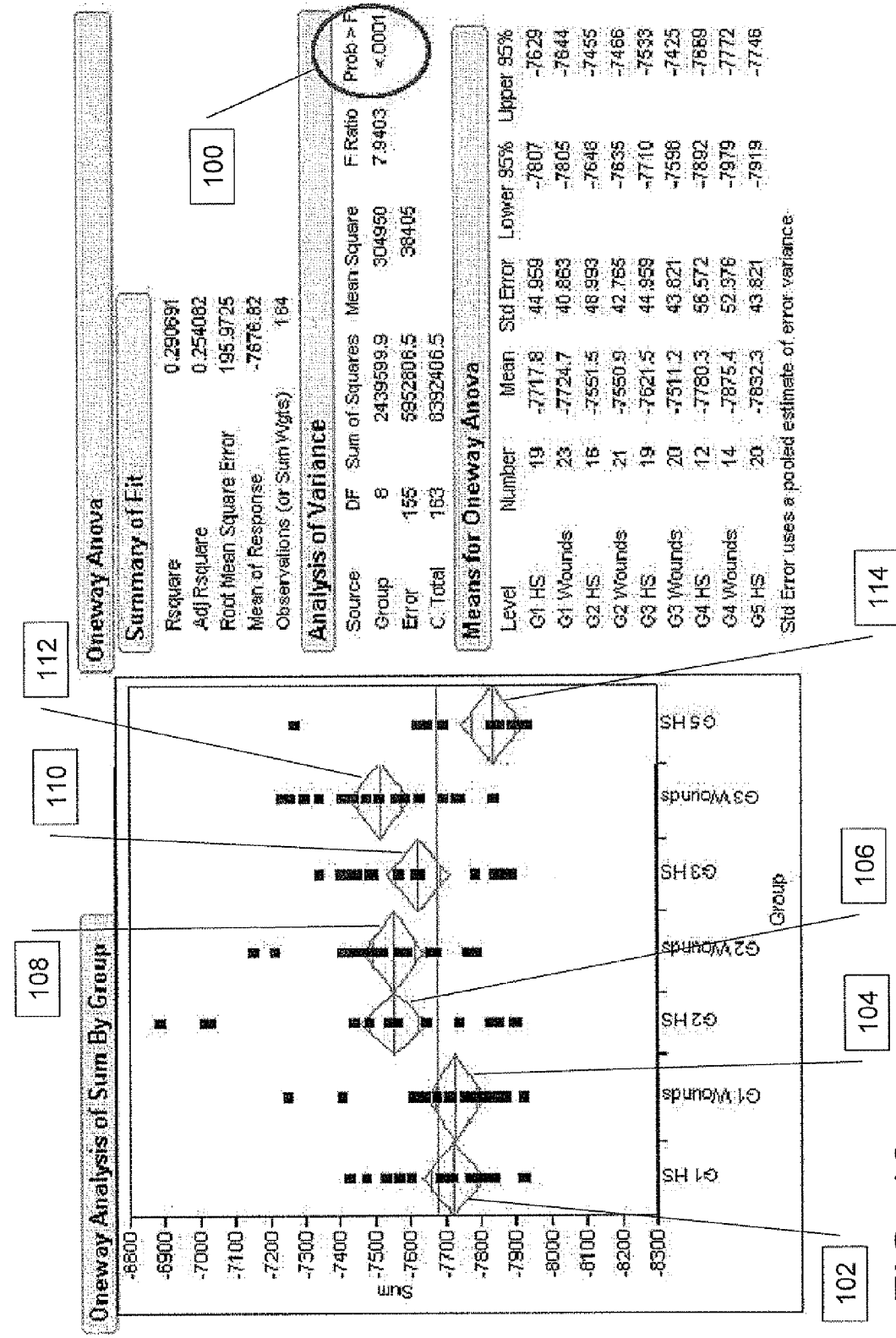
FIG. 10 is a chart that summarizes the statistical analysis/comparisons between the groups.
Figure 12C:
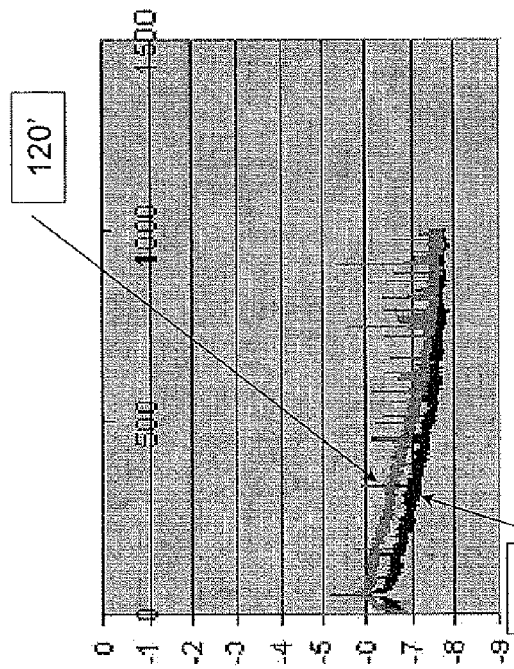
Figure 12E:
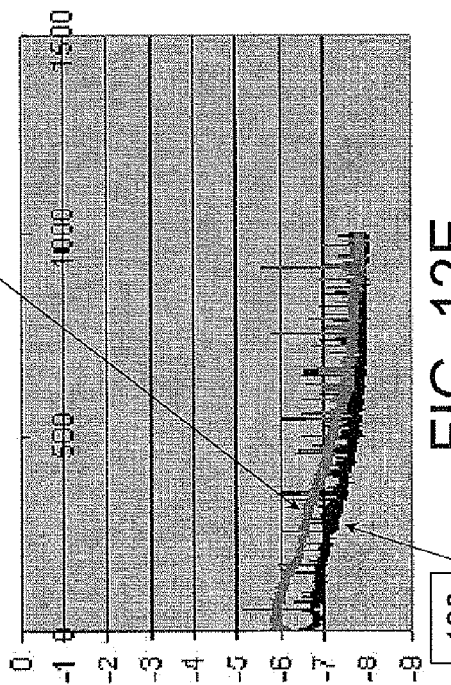
Figure 12B:
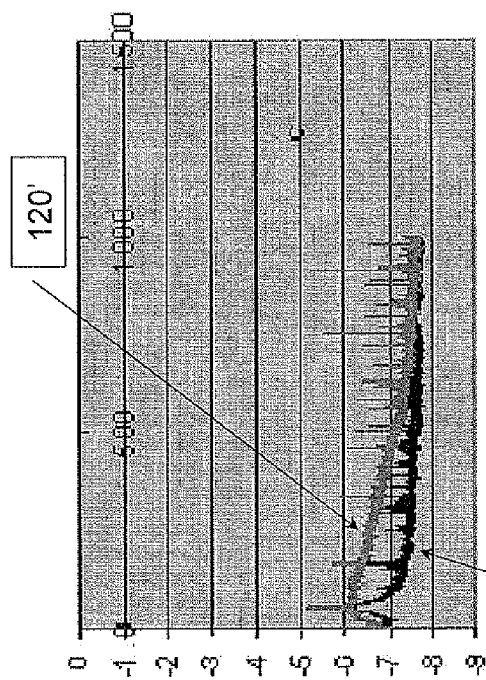
Figure 12D:
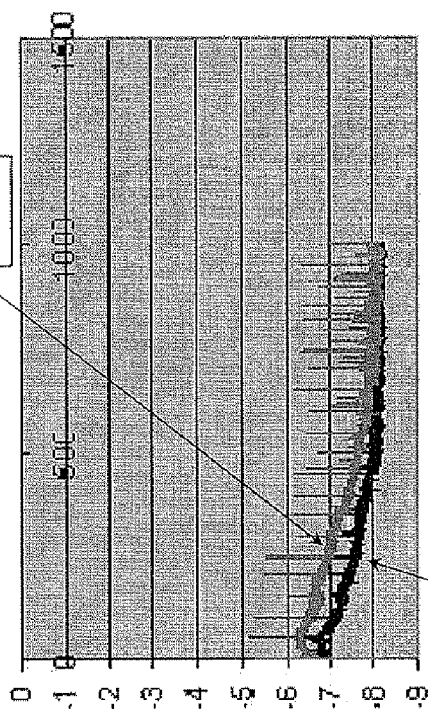

FIG. 10 summarizes the statistical analysis/comparisons between the groups. The F value 100 which is <0.0001, shows the significance of the differences between wounds in the stopped state 104, worsening state 108 and healing state 112 in comparison to the baseline healthy subjects 114. The chart also shows that the mean values of contralateral healthy limb 102, 106 and 110 for each group respectively can be used as a marker for wound prognosis. It should be noted that while the mean values of worsening 108 and healing 112 wounds are close to each other, their relationship to the mean values of their respective contralateral healthy limbs 106 and 110 are noticeably different.

FIG. 11 is a graph the FFT level around a chronic wound 110 and the FFT level for the contralateral no injured tissue 110' for a group of subjects having wounds in a worsening state without injection. FIGS. 12A-12E are graphs the FFT level around a chronic wound 120 and the FFT level for the contralateral non-injured tissue 120' for five individual subjects having wounds in a worsening state due to infection. It will be readily appreciated that in the group having wounds in a worsening state without injection (FIG. 11) the FFT level around the chronic wound 110 and the FFT level for the contralateral non-injured tissue 110' are substantially the same and the line for the FFT level around the chronic wound 110 is obscured by the line FFT level for the contralateral non-injured tissue 110'. In contrast, the FFT level around the chronic wound 120 and the FFT level for the contralateral non-injured tissue 120' for the five individual subjects having wounds in a worsening state due to infection (FIGS. 12A-12E) are both statistically and visually quite different. Therefore, according to the teaching of the present invention, it is possible to distinguish wounds in a worsening state due to infection from wounds in a worsening state without injection.

Therefore, the present invention includes, as illustrated in the flowchart of FIG. 13 a method of determining if a worsening wound in living human and animal tissue is infected. The method including the steps of:

13-1 Detecting and recording a first electrical signal in and around an area of the target tissue a second electrical signal in and around contralateral tissue, the first and the second electrical signals being a stochastic signals.

13-2 Transforming the first and the second electrical signals into a voltage versus frequency spectra using a Fast Fourier Transform (FFT) algorithm.

13-3 Comparing a graph of a resultant FFT level of the first electrical signal to an FFT level of the second electrical signal and at least one graph of a baseline FFT level of wounds in a worsening state without infection.

13-4 Determining the presences of infection in the target tissue based on the comparison.

FIG. 14 illustrates a method of the present invention for detecting the current state of living human and animal target tissue. The method includes the steps of:

14-1 Detecting and recording an electrical signal in and around an area of the target tissue, the electrical signal being a stochastic signal.

14-2 Transforming the stochastic signal into a voltage versus frequency spectra using a Fast Fourier Transform (FFT) algorithm.

14-3 Comparing a graph of a resultant FFT level of the target tissue to at least one graph of a baseline FFT level.

14-4 Determining a current state of the target tissue based on said comparison.

FIG. 15 illustrates a first method of the present invention for determining a prognosis for wounds in living human and animal target tissue. The method includes the steps of:

15-1 Detecting and recording a first electrical signal in and around an area of the target tissue a second electrical signal in and around contralateral tissue, the first and the second electrical signals being a stochastic signals.

15-2 Transforming the first and the second electrical signals into a voltage versus frequency spectra using a Fast Fourier Transform (FFT) algorithm.

15-3 Comparing a graph of a resultant FFT level of the first electrical signal to at least one graph of a baseline FFT level and an FFT level of the second electrical signal.

15-4 Determining a prognosis of the target tissue based on the comparison.

FIG. 16 illustrates a second method of the present invention for determining a prognosis for wounds in living human and animal target tissue. The method includes the steps of:

16-1 Detecting and recording an electrical signal in and around an area of the target tissue, said electrical signal being a stochastic signal.

16-2 Transforming said stochastic signal into a voltage versus frequency spectra using a Fast Fourier Transform (FFT) algorithm.

16-3 Comparing a graph of a resultant FFT level of the target tissue to FFT level referenced markers.

16-4 Determining a current state of the target tissue based on said comparison.

It will be appreciated that the above descriptions are intended only to serve as examples and that many other embodiments are possible within the spirit and the scope of the present invention.

What is claimed is:

1. A method of determining the presence of infection in a worsening wound in live target tissue of a patient, the method comprising:

detecting and recording (a) first endogenous electrical signal in and around an area of the live target tissue and (b) second endogenous electrical signal in and around contralateral tissue, said first and said second endogenous electrical signals being stochastic signals that are generated by the body of the patient itself;

transforming said first and said second endogenous electrical signals into a first and a second voltage versus frequency spectra, respectively, using a Fast Fourier Transform (FFT) algorithm;

comparing (i) said first voltage versus frequency spectrum, (ii) said second voltage versus frequency spectrum, and (iii) at least one baseline voltage versus frequency spectrum of wounds in a worsening state without infection; and determining a presence of infection in the target tissue based on said comparison.

2. The method according to claim 1, wherein said detecting and recording is detecting and recording an alternating current (AC) over time.

3. The method according to claim 2, wherein each of said first, second and baseline voltage versus frequency spectra is between 0 to 5000 Hz.

4. The method according to claim 3, wherein each of said first, second and baseline voltage versus frequency spectra is between 0 to 3000 Hz.

5. The method according to claim 4, wherein each of said first, second and baseline voltage versus frequency spectra is between 0 to 2000 Hz.

6. The method according to claim 5, wherein each of said first, second and baseline voltage versus frequency spectra is between 0 to 1000 Hz.

7. The method according to claim 1, wherein the wound is a chronic wound.

8. The method according to claim 1, wherein said baseline voltage versus frequency spectrum of wounds in a worsening state without infection is of one or more other patients.

9. The method according to claim 1, further comprising:
providing data regarding the presence of infection in the target tissue to a device configured to transmit an alternating current to the target tissue; and
transmitting, to the target tissue, an alternating current having a frequency spectrum based on said data.

* * * * *